United States Patent
Hadjar et al.

(10) Patent No.: US 9,696,208 B2
(45) Date of Patent: Jul. 4, 2017

(54) INTERFEROMETRIC DEVICE AND CORRESPONDING SPECTROMETER

(71) Applicant: Universite de Technologie de Troyes, Troyes (FR)

(72) Inventors: Yassine Hadjar, Paris (FR); Mikael Renault, Troyes (FR); Aurélien Bruyant, Troyes (FR); Sylvain Blaize, Troyes (FR)

(73) Assignee: UNIVERSITE DE TECHNOLOGIE DE TROYES, Troyes (FR)

( * ) Notice: Subject to any disclaimer, the term of this patent is extended or adjusted under 35 U.S.C. 154(b) by 0 days.

(21) Appl. No.: 14/895,739

(22) PCT Filed: Jun. 6, 2014

(86) PCT No.: PCT/FR2014/051365
§ 371 (c)(1),
(2) Date: Dec. 3, 2015

(87) PCT Pub. No.: WO2014/195655
PCT Pub. Date: Dec. 11, 2014

(65) Prior Publication Data
US 2016/0123814 A1    May 5, 2016

(30) Foreign Application Priority Data
Jun. 6, 2013  (FR) .................. 13 55223

(51) Int. Cl.
*G01B 9/02* (2006.01)
*G01J 3/453* (2006.01)
*G01N 21/552* (2014.01)

(52) U.S. Cl.
CPC ............. *G01J 3/453* (2013.01); *G01J 3/4532* (2013.01); *G01N 21/553* (2013.01); *G01J 2003/4538* (2013.01)

(58) Field of Classification Search
CPC ........ G01J 3/453; G01J 3/4531; G01J 3/4532; G01J 3/0205; G01J 3/021; G01J 3/0213;
(Continued)

(56) References Cited

U.S. PATENT DOCUMENTS 6,128,075 A * 10/2000 Brierley .................... G01J 3/45
  250/340
8,506,887 B2 * 8/2013 Rong ..................... G01N 21/55
  356/446
(Continued)

FOREIGN PATENT DOCUMENTS

FR       2 929 402       10/2009

OTHER PUBLICATIONS

International Search Report dated Sep. 4, 2014 out of corresponding PCT Application No. PCT/FR2014/051365 (6 pages).
(Continued)

*Primary Examiner* — Kara E Geisel
*Assistant Examiner* — Jonathon Cook
(74) *Attorney, Agent, or Firm* — Brinks Gilson & Lione; G. Peter Nichols

(57) ABSTRACT

An interferometric device: includes a separator, for separating a collimated beam (F0) into first (F1) and second (F2) incident beams; at least one transducer; and a transparent optical system, including at least three planar diopters (D1, D2, D3). The the transducer is based on plasmon resonance and in contact with the diopter (D1); the diopter (D2) has a network of nanostructures; the optical system and the separator being configured such that the beam (F1) and the beam (F2) undergo total internal reflection on the diopter (D1) and on the diopter (D3), respectively, prior to interfering on the diopter (D2) by total internal reflection and to forming an interferogram in which the central fringe is located at a convergence point (ZOPD).

10 Claims, 3 Drawing Sheets

Figure 1:
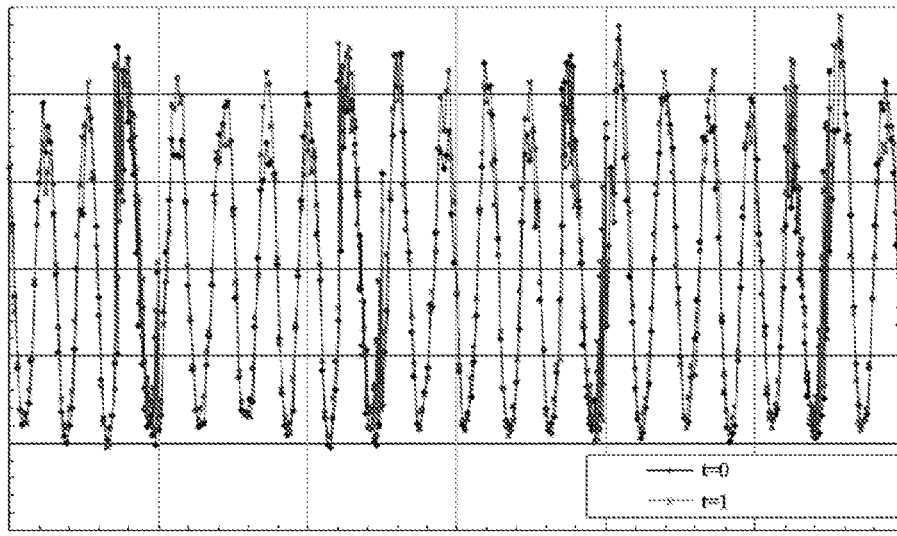

(58) Field of Classification Search
CPC ............... G01J 3/0256; G01J 3/0259; G01J 2003/4538; G01J 9/0246; G01N 21/552; G01N 21/553; G01N 21/554; G01N 2021/212; G01N 2021/213; B82Y 15/00; B82Y 20/00
USPC ........................................................ 356/451
See application file for complete search history.

(56) References Cited

U.S. PATENT DOCUMENTS

| | | | |
|---|---|---|---|
| 2009/0237647 A1* | 9/2009 | Azimi | G01J 3/02 356/51 |
| 2010/0079754 A1* | 4/2010 | Kuo | G01J 3/02 356/301 |
| 2011/0292394 A1 | 12/2011 | Wu | |
| 2012/0293860 A1* | 11/2012 | Gundlach | G01N 21/552 359/351 |
| 2015/0116720 A1 | 4/2015 | Hadjar | |

OTHER PUBLICATIONS

Written Opinion dated Sep. 4, 2014 out of corresponding PCT Application No. PCT/FR2014/051365 (6 pages).
Article, Renault et al., "Bidimensional near-field sampling spectrometry", Optics Letters, The Optical Society of America, vol. 35, No. 19, Oct. 1, 2010, pp. 3303-3305, US-ISSN 0146-9592, Publication Info: XP001557845.

* cited by examiner

INTERFEROMETRIC DEVICE AND CORRESPONDING SPECTROMETER

More precisely, according to a first of its subjects, the invention relates to an interferometric device comprising:
- a splitter (20), configured to split a collimated incident light beam (F0) into a first incident beam (F1) and a second incident beam (F2);
- a transparent optical block (10) comprising a set of at least three plane faces (D1, D2, D3), and
- at least one transducer (13) configured to carry out a transduction based on surface plasmon resonance and in contact with the first face (D1).

It is essentially characterized in that
- the second face (D2) carries a network of nanostructures at the level of which the first incident beam (F1) and the second incident beam (F2) are liable to interfere and to then form an interferogram whose central fringe is situated at a defined convergence point (ZOPD);
- the optical block (10) and the splitter (20) being configured so that the first incident beam (F1) undergoes at least one total internal reflection on the first face (D1) and the second incident beam (F2) undergoes at least one total internal reflection on the third face (D3) before they interfere on the second face (D2) under total internal reflection;
- the interferometric device further comprising a computer (50), configured to simultaneously compute the spectral distribution of the amplitude and the relative phase of the incident light beam (F0) that has interacted with at least one transducer (13, 14) by the first incident beam (F1) or by the second incident beam (F2).

Thanks to the invention, it is thus possible to have access to a phase measurement. In particular, the invention makes it possible to solve a large number of technical problems related to phase measurement in surface plasmon resonance (SPR) systems.

In particular, the invention comprises a static and compact SPR device providing direct access to the phase.

Thus, thanks to the invention, and in contrast to the prior art solutions which comprise a dynamic SPR device, here there is:
- no need an electro-optical enslavement;
- no need an ultra-stabilized laser sources coupled to optical acousto transducers;
- no need two beams of orthogonal polarization in order to carry out a relative phase measurement;
- etc.

In one embodiment, a second transducer (14) is further provided, said second transducer (14) being in contact with the second face (D2).

In one embodiment, the first face supports a plurality of transduction zones (131, 132, 133, 134), each transduction zone (131, 132, 133, 134) comprising an individual transducer.

In one embodiment, the second face (D2) comprises a plurality of interference zones (Z1, Z2, Z3, Z4), each interference zone (Z1, Z2, Z3, Z4) comprising a set of nanostructures, the optical block (10) being configured so that a given transduction zone (131, 132, 133, 134) is disposed in correspondence with a given interference zone (Z1, Z2, Z3, Z4), so that the total internal reflection of the first incident beam (F1) on a given transduction zone (131, 132, 133, 134) interferes with the second incident beam (F2) in a given interference zone (Z1, Z2, Z3, Z4).

In one embodiment, the optical block (10) is an assembly or a molding equivalent to the assembly of a first isosceles right prism (11) with a second isosceles right prism (12), in which the length of a side of the second isosceles right prism (12) is equal to half the length of the hypotenuse of the first isosceles right prism (11), the second prism (12) being assembled by one of its sides on a half of the hypotenuse of the first prism (11) so that the hypotenuse of the second prism (12) is parallel to a side of the first prism (11), and so that a cross-section of the optical block (10) thus produced is inscribed in a square.

In one embodiment, the splitter is a splitter cube (20), produced by assembly or by a molding equivalent to the assembly of a first isosceles right prism (21) and of a second isosceles right prism (22) identical to the first isosceles right prism (21), the first isosceles right prism (21) and the second isosceles right prism (22) being assembled by their hypotenuse, one of which is metallized.

In one embodiment, the position of the central fringe of the interferogram at the convergence point (ZOPD) is determined by construction of the optical block (10) as a function of the dimensions of the first right isosceles prism (11) and of the second right isosceles prism (12) of said optical block (10).

According to another of its subjects, the invention relates to a spectrometer comprising a device according to the invention, a light source (1) configured to emit said incident light beam (F0), and comprising an optical sensor (30) disposed opposite the nanostructures of the second face (D2) and configured to catch the diffusion of the interferogram resulting from the interference of the first incident beam (F1) and of the second incident beam (F2).

In one embodiment, the spectrometer further comprises
- a computer (50),
- two power-meter (40a, 40b), and
- a memory in which the value of the power (P_mes($\lambda$)) measured by the second power-meter (40b) is recorded simultaneously with the value of the reference power output by the source (1) measured by the first power-meter (40a); and in which
- the computer (50) is configured to
  - determine the incident spectrum (F0) by Fourier transform of the interferogram caught by the optical sensor (30) which measures the luminous power diffused by each nanostructure of the network of nanostructures of the second face (D2) and store it in a memory;
  - compute the reflectivity (R_spr($\lambda$)) according to the equation R_spr($\lambda$)=2*P_mes($\lambda$)/P_F0(A), with P_F0($\lambda$) the power of the incident beam (F0) emitted by the light source (1) which is known or measured by the first power-meter (40a).

In one embodiment, the light source (1) is monochromatic, and
the computer (50) is configured to compute the phase shift ($\phi(\lambda)$) of the first beam (F1) by comparing I(t1) and I(t0) two values recorded in a memory and corresponding to the intensity distribution on the plane (xoy) of the interferogram obtained by causing the first incident beam (F1) and the second incident beam (F2) to interfere on the second face (D2), at a time t1 and a time t0 respectively.

In one embodiment, the light source (1) is broadband, and the computer (50) is configured to compute the spectrum of the source filtered by the reflection coefficient (R_spr($\lambda$)) of the transducer (13).

Figure 2A:
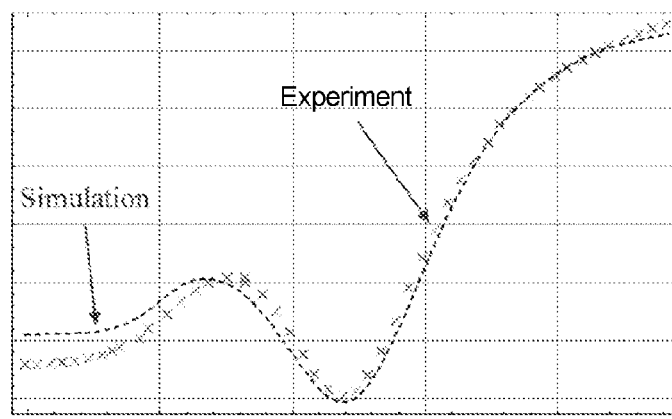
Figure 2B:
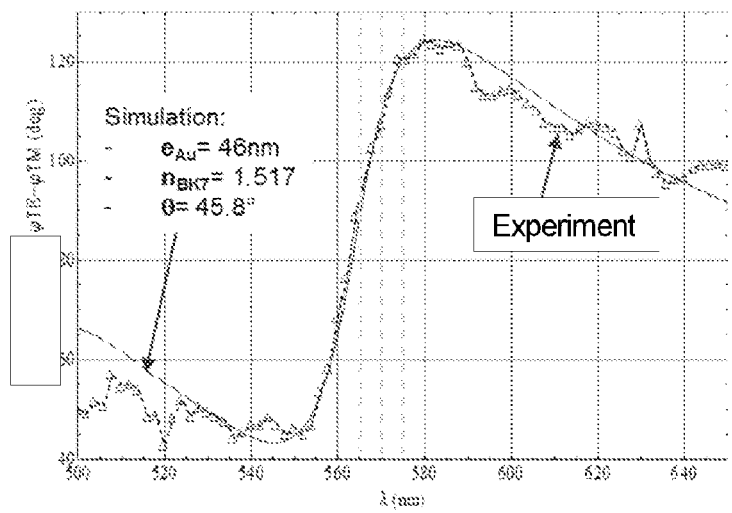
Figure 3:
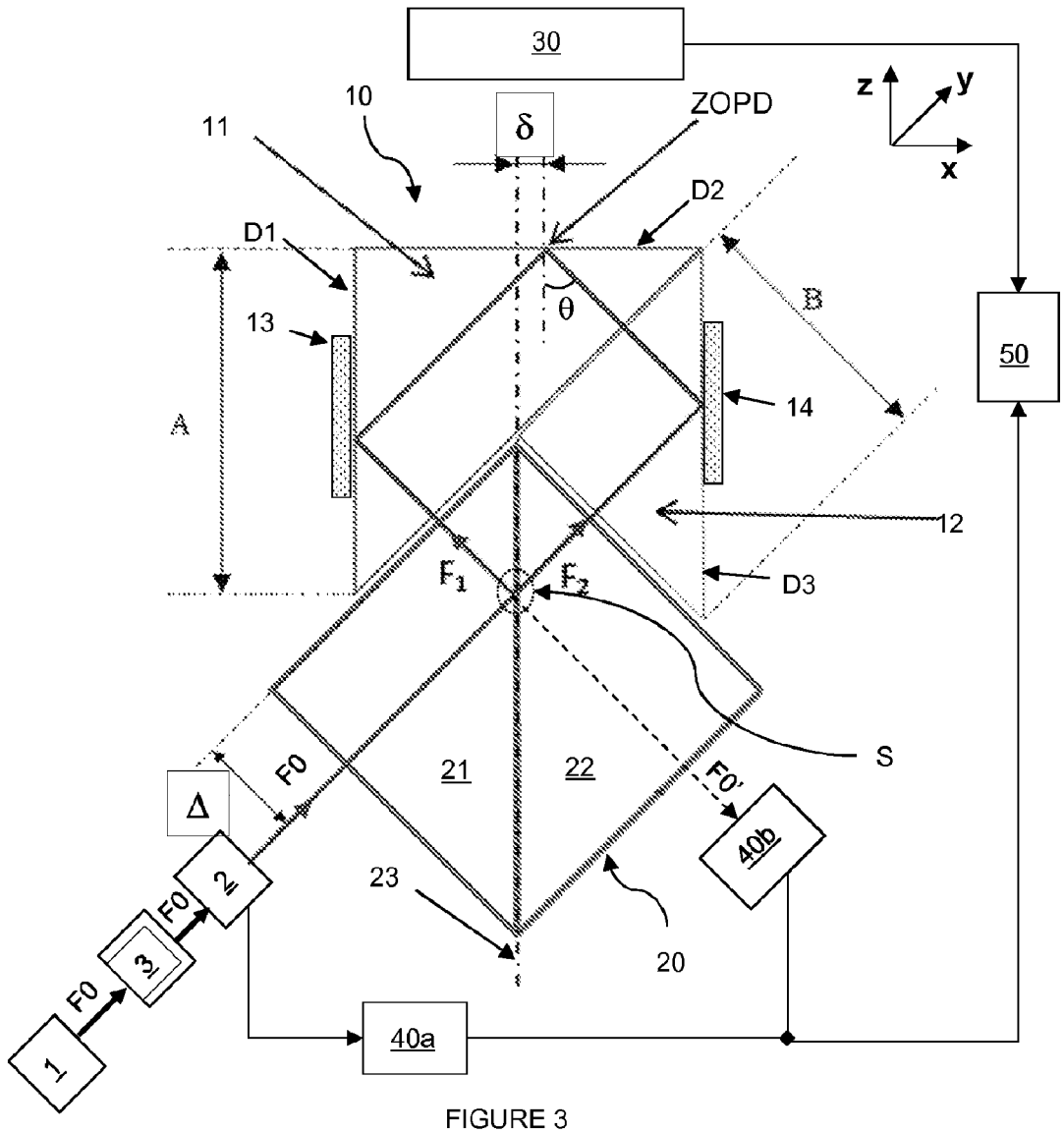
Figure 6:
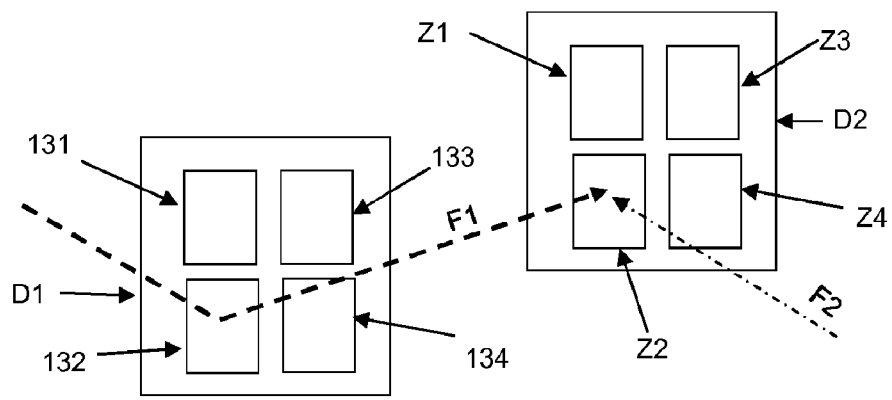
Figure 4:
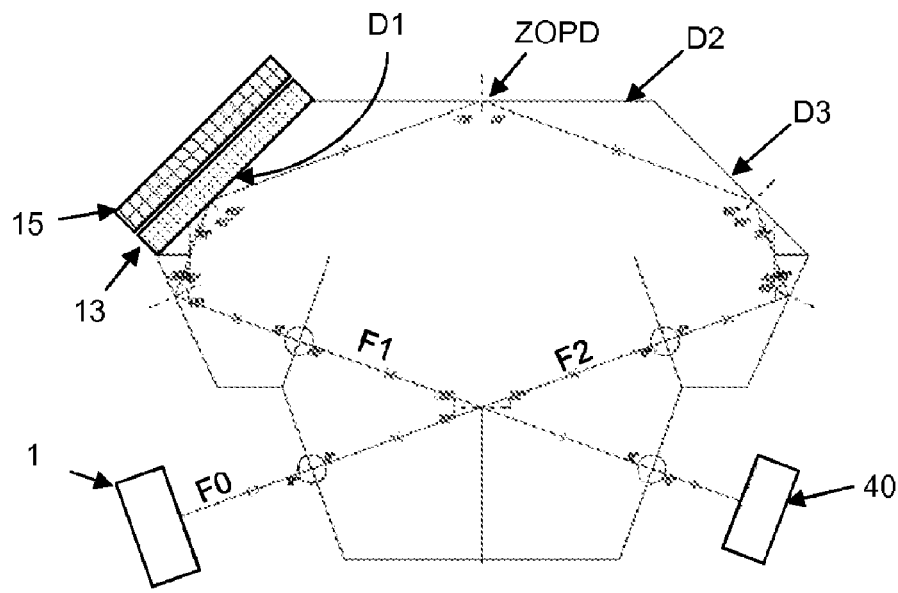
Figure 5:
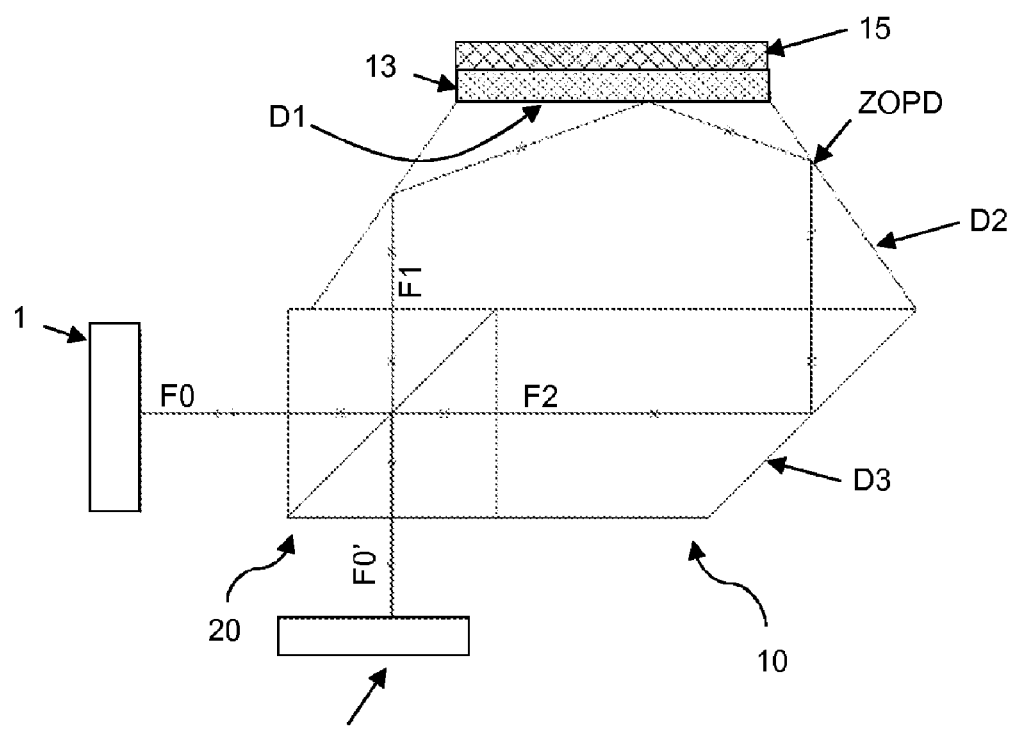

Other characteristics and advantages of the present invention will be more clearly apparent on reading the following description given by way of illustrative and nonlimiting example and with reference to the appended figures in which:

FIG. 1 illustrates, for a given wavelength, two truncated interferograms, measured between two instants, and produced with a device according to an embodiment of the invention, FIG. 2a illustrates the comparison of the variation of the reflection coefficient as a function of the wavelength between a simulation and an experiment with a device according to an embodiment of the invention, FIG. 2b illustrates the comparison of the variation of the phase shift introduced by the reflection of the first beam F1 on the transducer under TM polarization, by taking as reference phase the phase under TE polarization, as a function of the wavelength between a simulation and an experiment with a device according to an embodiment of the invention;

FIG. 3 illustrates an embodiment of an interferometric device according to the invention, FIG. 4 illustrates an embodiment of an interferometric device according to an embodiment with fluidic micro cell, FIG. 5 illustrates another embodiment of an interferometric device according to an embodiment with fluidic micro cell, and FIG. 6 illustrates a functionalization of the surface of the diopter D1 comprising a plurality of transducers.

In its principle, the invention is aimed at analyzing, based on spectrometry, the properties or the nature of biological or chemical compounds included in a fluid, that is to say a liquid or a gas, based on the spectrometry.

For this purpose, we carry out the interference of two incident beams F1 and F2, only one of which is disturbed by said fluid.

With reference especially to FIG. 3, a light source 1, when it is active, generates an incident light beam F0, termed the "incident beam" for conciseness.

In one embodiment, the incident beam F0 is monochromatic.

In another embodiment, the incident beam F0 is polychromatic, and in this instance, in white light.

The particular features relating to each of these two embodiments are described later.

Preferably, a collimator 2 is provided, making it possible to obtain a beam of parallel rays arising from the incident beam.

For example the collimator is a system of lenses which is known to the person skilled in the art.

Preferably, the collimator 2 further comprises a splitter which taps off a few percent of the power of the incident beam F0. This tapping-off makes it possible to control the power of the light source, in this instance a laser, with the aid of a first power meter 40a, in this instance a calibrated photodiode, and to normalize the power measurement by the second power meter 40b described later.

It is possible to provide an optical fiber (not illustrated) between the light source and the collimator 2.

It is also possible to provide a polarizer 3, configured to polarize the incident beam F0, in the case where the source is not polarized, under TM polarization (electric field in the incidence plane xoz) or TE polarization (magnetic field in the incidence plane xoz), in particular when the transducer 13 described later is configured to carry out a transduction based on plasmon resonance (SPR). Preferably, the polarizer is situated before the element which taps off a part of the beam F0 to the power-meter 40a, so as to take account of the intensity fluctuations related to polarization effects of the source, in this instance a laser.

Splitter

A splitter is provided, preferably downstream of the collimator, configured to split the incident beam F0 into a first incident beam F1 and a second incident beam F2.

Preferably, the ratio of the splitter (proportion between the reflected beam and the refracted beam) is chosen so as to maintain the highest possible contrast of the fringes by balancing the powers of the beams F1 and F2 at the level of the diopter D2. For example, when the transducer 13 is configured to carry out a transduction based on plasmon resonance, it is possible to choose a 10/90 splitter in such a way as to increase the power of the beam F1 with respect to the beam F2 so as to compensate the strong absorption of the photons which excite the surface plasmons to resonance. With another type of transducer 13, it is possible to provide a 50/50 splitter.

The splitter can be a splitter plate, the metallization of a diopter (for example a semi-reflecting mirror), or a splitter cube 20, in particular such as described hereinbelow.

In the case of a thin splitter plate, it is necessary to take account of the shift of the beam transmitted related to the thickness of the plate in the expression for $\Delta$ and $\delta$ which are described later.

In one embodiment, provision is indeed made for the splitter to be a splitter cube 20, produced for example by assembly of a first isosceles right prism 21 and of an identical second isosceles right prism 22, assembled by their hypotenuse, one of which acts as splitter, for example by metallization thereof.

Thanks to this configuration, assembly of the splitter cube 20 is easy and fabrication inexpensive since right isosceles prisms are the commonest prisms and are very affordable in price.

Optical Block

An optical block 10 is also provided, making it possible to cause the two incident beams F1 and F2 arising from the splitter to interfere.

Optical block is intended to mean a solid and transparent element with preferably isotropic optical properties and comprising a set of at least three plane surfaces, each plane surface having a plane diopter function when said plane surface of said optical block is placed in a medium of different refractive index from that of said block. Here, therefore, the terms "surface", "side" or "face" of the optical block, or "diopter", are akin.

In this instance, the optical block 10 comprises a first diopter D1, a second diopter D2 and a third diopter D3.

In FIG. 3, the first diopter D1 is parallel to the third diopter D3 and perpendicular to the second diopter D2. But the realization of an optical block is not limited to this configuration alone.

Diopter is intended to mean a surface separating two unequally refringent transparent media. In this instance, a surface separating a first medium, in this instance said optical block, from a second medium whose refractive index is different from that of said first medium, in this instance a fluid. The fluid can be a gas, for example air, any other gas or mixture of gases; or a liquid, placed in contact with a transducer 13 for example by way of a micro fluidic cell 15. In all cases, the second medium must exhibit a lower refractive index than that of the optical block.

For example the optical block 10 can be made of glass or synthetic material whose refractive index is close to that of glass. The optical block can be molded or assembled for example thanks to a cement (molecular, UV etc.) and an index gel.

Provision is made for the first diopter D1 of the optical block 10 to support a transducer 13 configured to carry out a transduction based on plasmon resonance, that is to say the resonant absorption of photons by the electrons of a fine metallic layer. The photons of a light source, that is to say the beam F1, excite plasmonic waves which propagate on the surface of the metallic layer. This excitation, in particular the resonant frequency of this excitation, is very sensitive to the variation of the refractive index of the fluid medium in contact with the metallic layer. Measurement of the properties of the light that has interacted with the transducer 13 then makes it possible to ascertain the variation of the refractive index in the vicinity of the metallic layer. This variation of index is related essentially to the adsorption of specific molecules (chemical or biological compounds) that it is sought to detect. SPR (Surface Plasmon Resonance) sensors are among the most sensitive and also make it possible to carry out dynamic measurements of chemical or biological reactions.

For example the transducer is a thin metallic layer, in this instance of gold, evaporated on the surface of a diopter D1 of the optical block 10.

The transducer 13 can comprise, in addition to the fine layer of metal, elements liable to combine with complementary biological or chemical compounds that it is sought to detect and that are contained in a fluid in contact with said thin metallic layer. This bio-chemical surface functionalization makes it possible to carry out so-called selective measurements.

Provision is made for the second diopter D2 of the optical block 10 to support a network of nanostructures which is centered around the convergence point ZOPD, thereby allowing the detection of the interferogram by an optical sensor 30, for example a CCD camera, disposed opposite the nanostructures.

Provision is made for the third diopter D3 of the optical block 10 to be left in the open air.

Provision may be made for the third diopter D3 of the optical block 10 to support a transducer 14, different from the transducer 13 supported by the first diopter D1. In this case, the effects of the interactions between the biological or chemical compounds that it is sought to detect and the transducer 14 are known, so as to allow a differential analysis of the effects of the interactions of the biological or chemical compounds that it is sought to detect with between on the one hand the first diopter D1 carrying the transducer 13 and on the other hand the third diopter D3 optionally carrying the transducer 14.

In one embodiment, provision is made for the optical block 10 to be an assembly of a first isosceles right prism 11 with a second isosceles right prism 12, in which the length of a side of the second isosceles right prism 12 is equal to half the length of the hypotenuse of the first isosceles right prism 11, that is to say that the length of the hypotenuse of the second isosceles right prism 12 is equal to the length of a side of the first isosceles right prism 11.

In this case, the second prism 12 is assembled by one of its sides on a half of the hypotenuse of the first prism so that the hypotenuse of the second prism 12 is parallel to a side of the first prism 11, and so that a cross-section of the optical block 10 thus produced is inscribed in a square.

Thanks to this configuration, it is possible to insert the splitter into the space left free between the other half of the hypotenuse of the first prism 11 and the other side of the second prism 12 of the optical block. This being particularly advantageous with the splitter cube described hereinabove.

In this case, the splitter cube 20 is assembled by one of its faces between the free half of the hypotenuse of the first prism 11 of the optical block and the free side of the second prism 12 of the optical block. Thus, the plane 23 of the splitter, which is the prolongation of the diagonal of the splitter cube, passes through the center of the hypotenuse of the first prism 11 (which is also the vertex of the second prism 12 of the optical block) and the center of the second diopter D2.

Provision may be made for the first isosceles right prism 11 of the optical block to be identical to one of the prisms 21, 22 of the splitter cube 20.

The optical block 10 obtained by assembly, optionally combined with the splitter cube 20, can also be obtained by molding. The optical block, optionally combined with the splitter cube, advantageously exhibits a plane of symmetry passing through the plane 23 of the splitter, illustrated by dashes in FIG. 3.

One of the diopters of the optical block, in this instance the second diopter D2, carries nanostructures which make it possible to sample spatially (in the plane xoy) an interferogram produced by the interference of the first beam F1 under total internal reflection on this diopter with the second beam F2 under total internal reflection on this same diopter, as described in the applicant's patent FR2929402. The central fringe of the interferogram, and which corresponds to the convergence point ZOPD, is ideally centered on the network of nanostructures.

The optical block 10 is configured so that the first beam F1 undergoes a total internal reflection on the diopter carrying the transducer before arriving at the convergence point ZOPD.

The angle between the first diopter D1 and the second diopter D2 can be a right angle as illustrated in FIG. 3, or different, as illustrated in FIG. 4 or FIG. 5.

The convergence point ZOPD is also called the point of zero path length difference and corresponds to the position of the central fringe of the interferogram forming on the diopter carrying the nanostructures D2. It is recalled here that a beam consists of rays. With a collimator, the geometric structure of a collimated beam F0 has cylindrical symmetry with an axis of symmetry. At the level of the convergence point ZOPD, the rays of the beams F1 and F2 coincide with the axes of symmetry of said beams F1 and F2. The rays which do not coincide with the axis of symmetry interfere with phase shifts which depend on their distance with respect to the axis of symmetry of the beam. This is what gives the interference pattern with intensity maxima and minima on either side of the central fringe.

The position of the central fringe of the interferogram ZOPD can be controlled and fitted by construction, as a function of the dimensions of the first right isosceles prism 11, of the second right isosceles prism 12 of the optical block 10. It is possible to provide furthermore as a function of the point of entry of the incident beam F0 into the splitter cube 20, that is to say of the position of the point S along the plane 23.

It is possible to define:
A the length of one of the sides of the first right isosceles prism 11 of the optical block, in this instance the length of the diopter D1;
B the length of one of the sides of the second right isosceles prism 12 of the optical block, in this instance the side assembled with the splitter cube 20;

Δ the distance between the incident beam F0 and the face of the splitter cube 20 parallel (in this instance merged) with the plane passing through the hypotenuse of the first right isosceles prism 11; and δ the distance between the point ZOPD corresponding to the position of the central fringe of the interferogram (for which the path length difference is zero) on the diopter D2 carrying the nanostructures and the plane passing through the plane 23 of the splitter, in this instance the diagonal of the splitter cube 20 parallel to the face containing the diopter D1 (and D3), and passing through the middle of said face of said diopter D2.

As set forth hereinbelow, the diagonal passes through the middle of the diopter D2 only in the particular case where the sides A and B satisfy $A=B\sqrt{2}$ (symmetric configuration). In FIG. 3 where a more general example which is not symmetric is illustrated, the plane 23 of the splitter does not pass through the middle of the diopter D2.

Preferably, the incident beam F0 is always parallel to the hypotenuse of the prism 11.

By definition, the optical paths of the two beams F1 and F2 are equal at the convergence point ZOPD. The convergence point ZOPD belongs to the plane containing the second diopter D2. In the particular case where A and B satisfy these two conditions, the length of a side of the second isosceles right prism 12 (that is to say B) is equal to half the length of the hypotenuse of the first isosceles right prism 11 ($H=A\times\sqrt{2}$; with H the hypotenuse of the prism), which amounts to writing: $B=(H/2)=A/\sqrt{2}$, we then have a plane of symmetry which contains the separating diagonal of the cube. Consequently, the convergence point ZOPD must belong to this plane of symmetry, that is to say δ=0.

We thus have:

$$\Delta = A/\sqrt{2} - B/2 \text{ and}$$

$$\delta = B/\sqrt{2} - A/2$$

Preferably, the refractive index of the first prism 11 and of the second prism 12 of the optical block is the same as that of the splitter cube 20. This making it possible to control the optical paths by geometric construction and avoid back-reflections (see multiple reflections) related to the passage of the light through two media of different indices.

As set forth previously, beyond the cube 20, any splitter can be used in combination with the optical block 10. The person skilled in the art understands that the use of a splitter having a different refractive index from the refractive index of the optical block 10 can influence the optical path of at least one of the first beam F1 and second beam F2.

The advantage of cementing right isosceles prisms for the optical block 10 as well as for the splitter cube 20 resides in the ease of finding such prisms on the market and their relatively low cost. However, other shapes of optical blocks or of splitters can be produced, such as illustrated in FIGS. 4 and FIG. 5. These figures are not described subsequently, the person skilled in the art understands that the optical rules relating to the optical paths and to the total internal reflections for the first beam F1 and the second beam F2 must be complied with.

Manner of Operation

The light source 1 emitting the incident beam F0 can be monochromatic, optionally tunable, or a broadband source.

The incident beam F0 preferably arrives with normal incidence at the surface of the splitter cube 20.

The splitter splits the incident beam F0 at a splitting point S (FIG. 3) into a first incident beam F1 and a second incident beam F2.

Between the splitting point S and the convergence point ZOPD, provision is made for the optical path of the first incident beam F1 to be equal to the optical path of the second incident beam F2.

The angle of incidence of the incident beam F0 on the splitter is such that the incident beam F1 and the incident beam F2 undergo a total internal reflection on each diopter of the optical block.

Provision may be made for a plurality of total internal reflections of the incident beams F1 and F2 in the optical block 10, as illustrated in FIG. 4 and FIG. 5, with the proviso that the optical paths of the first incident beam F1 and of the second incident beam F2 are controlled so as to position the convergence point ZOPD at the center of the zone of detection of the interferogram. But the number of reflections influences the risk of loss of quality or of power of the optical signal transported by the incident beams F1 and F2.

Preferably, the number of total internal reflections between the splitting point S and the convergence point ZOPD is as restricted as possible for each incident beam F1 and F2.

In this instance, FIG. 3, for the first incident beam F1 provision is made for a single total internal reflection on the diopter D1 of the optical block 10, and then a total internal reflection at the convergence point ZOPD on the diopter D2 of the optical block 10 carrying the nanostructures. Likewise, for the second incident beam F2 provision is made for a single total internal reflection on the diopter D3 of the optical block 10, and then a total internal reflection at the convergence point ZOPD on the diopter D2 of the optical block 10 carrying the nanostructures.

After interference on the diopter D2:
the first incident beam F1 undergoes a total internal reflection on the diopter D3 of the optical block 10, and then a reflection on the splitter, identical to that undergone by the beam F0 to give the beam F0 and which is not a total internal reflection, before being recombined with the second incident beam F2 as an exit beam F0' on the second power-meter 40b; and the second incident beam F2 undergoes a total internal reflection on the diopter D1 of the optical block 10, and then a transmission and a reflection (loss in reflection toward the source 1) on the splitter. The transmitted part of the second incident beam F2 is recombined in S with the reflected part of the first incident beam F1 so as to constitute the exit beam F0', on the power-meter 40b.

In the case of a 50/50 splitter cube, the total power of the exit beam F0' is then equal to half the incident power F0 in the case where the losses in the optical elements are negligible. The other half of the power (the transmitted part of F1 and the reflected part of F2 in S) resumes toward the source 1.

Transduction

At the first diopter D1 of the optical block, the transducer 13 disturbs the evanescent wave generated by the first incident beam F1, thereby introducing a modification in amplitude and in phase of said first incident beam F1, according to a function of the reflection coefficient R(λ) and of the phase shift φ (λ), which is related to the transducer and to the incident wavelength.

The particular feature of the transducer is that the coefficients R and φ are very sensitive to the refractive index of the surrounding medium, this being the very principle of the operation of a transducer. A small variation of the environment is manifested by a modification of its refractive index which, in its turn, modifies the coefficients R and φ. The information on the state of the environment is thus obtained by measuring the optical quantities R and φ.

The determinations of R and of φ are totally independent. This is moreover one of the advantages of the solution proposed here, and which makes it possible to carry out a spectral measurement of R and φ simultaneously. All the SPR sensors have sole access either to φ, or to R. R may be dependent on λ (R(λ)) or dependent on the angle of incidence θ (R(θ)) (and in this case λ is fixed).

In this instance the amplitude of the incident beam F1 after total internal reflection on the diopter D1 carrying the transducer 13 is equal to $A\_F1(\lambda)^* \sqrt{R(\lambda)} \exp[i^*\phi(\lambda)]$, with $A\_F1(\lambda)$ the amplitude of the incident beam before total internal reflection on said diopter D1 carrying the transducer 13; the power or the intensity of a light beam being expressed as the squared norm of the amplitude.

This modification in amplitude and in phase of the beam F1 makes it possible to detect the biological or chemical compounds contained in a fluid in contact with the transducer 13, by measuring the variations of the reflection coefficient R(λ) and of the phase shift φ(λ) of said first incident beam F1 when it interferes with the beam F2.

The interferogram generated at the level of the diopter D2 carrying the nanostructures of the optical block is sensed by an optical sensor 30, in this instance a CCD camera, which transmits its information to computer 50, in this instance a computer equipped with computation software and a memory.

Computation of λ

It is possible thanks to the computer 50 to determine the incident spectrum F0 by Fourier transform of the interferogram sensed by the optical sensor 30 and thus to access the wavelength or wavelengths of the beam F0 which is(are) recorded in a memory.

In this instance, the wavelength is obtained by considering the norm of the Fourier transform of the interferogram sampled spatially according to the process described in patent FR2929402.

Computation of R

A power-meter 40b, for example a calibrated photodiode, makes it possible to measure the power of the beam (or equally signal) F0' at the output of the optical block 10 and of the splitter, by recombining the beams F1 and F2 having mutually interfered.

The measured power P_mes(λ) is a function of the power P_F0(λ) of the incident beam emitted by the light source 1, which is known or measured, and of the reflectivity R_spr (λ).

Reflectivity R_spr(λ) or reflection coefficient R(λ) is intended without distinction. In "R_spr(λ)", the index "_spr" applied to the reflection coefficient R(λ) simply signifies a particular transducer 13, in this instance of SPR type.

The computer 50 can then compute the reflectivity R_spr (λ), typically according to the equation R_spr(λ)=2*P_mes(λ)/P_F0(λ) for a monochromatic source 1 (see FIG. 2a).

The value of the reflection coefficient R(λ)=R_spr(λ) thus computed is recorded in a memory.

In the case where the source 1 is broadband, that is to say with a width greater than that of plasmon resonance, and a transducer 13 configured to carry out a transduction based on plasmon resonance, the advantage is that the measurement can be done in a single acquisition of the interferogram. In this case the second power meter 40b is not necessary. In this case, the measured spectrum (λ) is equal to the spectrum of the source (1), multiplied (filtered) by the reflectivity R_spr (λ).

It is possible to obtain the same result using a monochromatic source that is tunable around plasmon resonance, but in this case, an acquisition of the interferogram is necessary for each wavelength, as is done for the phase.

Computation of φ

Computation of phase φ is intended to mean the relative phase with respect to a reference phase.

In the case of a monochromatic source, the phase φ(λ) can be deduced directly by utilizing the interferogram measured and which is expressed according to the following formula:

$$I(x,\lambda,t0)=A0+B0\times Cos(2\pi x/T+\phi 0)$$

$$I(x,\lambda,t1)=A1+B1\times Cos(2\pi x/T+\phi 1)$$

A0 and A1 are offsets, B0 and B1 are the amplitudes or contrasts of the interference fringes. These coefficients are obtained, in a first step of the numerical processing, by applying a curve of fit to the recorded interferograms. This fit can be achieved in a conventional manner using a least squares method.

T is the period of the interference fringes and is expressed as $T=\lambda/(2\, n\, Sin(\theta))$ where n is the refractive index of the prism 11 and θ the angle of incidence of the beams F1 and F2 at the level of the diopter D2. Fitting the experimental interferograms I(λ, t0) and I(λ, t1) makes it possible to obtain the normalized functions:

$$Cos(2\pi x/T+\phi 0)=(I(x,\lambda,t0)-A0)/B0$$

and $$Cos(2\pi x/T+\phi 1)=(I(\lambda,t1)-A1)/B1$$

By summing the two normalized functions the normalized signal S is obtained which can be rewritten, using the trigonometric relation $Cos(P)+Cos(Q)=2\times Cos((P+Q)/2)\times Cos((P-Q)/2)$, in the following manner:

$$S(x,\lambda,t0,t1)=2\times Cos((\phi 1-\phi 0)/2)\times Cos(2\pi x/T+(\phi 0+\phi 1)/2)$$

In a second step of the numerical processing, provision is made to fit, by a least squares method, the normalized signal. This numerical fit gives the value of the amplitude Amp01 of the signal S, namely $Amp01=2\times Cos((\phi 1-\phi 0)/2$. Knowing Amp01, it is possible to deduce the value of the relative phase (φ1−φ0):

$$\phi 1-\phi 0=2\times ArcCos(Amp01/2)$$

As illustrated in FIGS. 2a and 2b, the present solution provides access to the reflectivity and to the relative phase by experimentally determining the transfer functions in amplitude and in phase of a transducer of SPR type consisting in this instance of a thin layer of gold deposited on the face of the prism corresponding to the diopter D1. In the case of FIG. 2b, the reference phase for each wavelength λ has been measured by considering a TE polarization (electric field perpendicular to the incidence plane i.e. E//OY). Indeed, the spectral response of an SPR layer is flat (no plasmon excitation under TE). The transfer function of an SPR layer is given by exciting the electrons with a TM polarization (electric field in the incidence plane). Taking the signal under TE as reference is customarily used in SPR sensors of this type. The experimental curve of FIG. 2b has been obtained by considering the interferograms I(x,λ,TE) and I(x,λ,TM) independently of the time (by considering that the interferograms are stable over time when nothing disturbs the transducer, in this instance in contact with the air and at a controlled temperature of 22° C.). For each wavelength (between 500 and 700 nm) two interferograms I(x, λ,TE) and I(x,λ,TM) are recorded and the signal processing described above is applied to determine φTE-φTM.

A first measurement of I is performed at an instant t0, the value I(t0) of which is recorded in a memory, and then a second measurement is performed at an instant t1, the value I(t1) of which is recorded in a memory.

The difference between these two values I(t1)−I(t0) makes it possible to compute the value of the phase $\phi(\lambda)$ which corresponds to the phase variation undergone by the beam F1 (and F2 in the case where the transducer 14 is considered) between the instants t0 and t1.

Experimental Results

FIG. 1 shows two truncated interferograms, for a given wavelength (in this instance 630 nm), measured between two instants, in this instance at 10 minute intervals.

The curves of FIG. 1 illustrate the spatial distribution along the axis (ox) of the intensity received by the optical sensor 30 around the convergence point ZOPD, in this instance according to a method described in patent FR2929402.

As illustrated in FIG. 1, the interferogram at t=1 is almost completely overlaid on the interferogram at t=0, thus showing the high stability of the interferometric device over time.

FIG. 2a illustrates the variation of the reflection coefficient $R(\lambda)$ as a function of the wavelength for a simulation compared with an experiment, in which the minimum of the curve corresponds to the maximum of absorption of the photons by the electrons of the SPR layer and defines the plasmon resonance wavelength. As illustrated, the transfer function in terms of intensity (reflectivity) of the SPR transducer has indeed been measured with the aid of the device proposed here, with very good agreement with the simulations. It is therefore entirely possible to use the device proposed as SPR sensor with interrogation in terms of intensity.

Surface Functionalization

In the particular case of a transduction of SPR or LSPR type (that is to say a nanostructured thin metal layer) which has the advantage of controlling the position of the plasmon resonance as a function of the size and the density of the nanostructures, provision may be made for the first diopter D1 to comprise a plurality of transduction zones, each zone comprising a specific chemical surface treatment, so that each zone can be considered to be an individual transducer. The position of each zone or each transducer is known.

For example, the transduction zones and the interference zones are disposed according to a matrix positioning (see FIG. 6).

Represented schematically in FIG. 6 is a view from above of the first diopter D1 comprising for this example four transduction zones. Each zone 131, 132, 133, 134 comprises a specific chemical surface treatment, preferably differing from one zone to the other, thereby allowing detection of multiple chemical or biological species.

In this case, provision is made to structure the sampling zone at the level of the second diopter D2 carrying the nanostructures, that is to say for the second diopter to comprise a plurality of interference zones. Each interference zone Z1, Z2, Z3, Z4 comprises a network of nanostructures. The position of each interference zone or of each network of nanostructures is known.

The optical block 10 is configured so that a given transduction zone is disposed in correspondence with a given interference zone, so that the total internal reflection of the first incident beam F1 on a given transduction zone can interfere with the second incident beam F2 only in a given interference zone. In FIG. 6, the transduction zone 132 is disposed in correspondence with the interference zone Z2 so that the beam F1, illustrated dashed, undergoes a total internal reflection on the transduction zone 132 and then interferes with the second beam F2 (not illustrated) in the interference zone Z2.

For example each transduction zone is configured to detect a given chemical or biological species.

In this embodiment where the first diopter D1 is functionalized, the incident beam F0 is monochromatic.

Other Advantages

Thanks to the invention, it is possible to obtain a compact system affording access simultaneously to the spectral distribution of the amplitude and the relative phase of the incident beam F0 that has interacted with at least one transducer 13, 14 by way of the beams F1 or F2.

Thanks to the invention, the two incident beams F1 and F2 interfere under extremely stable conditions (in this instance encapsulated in glass); that is to say that the interferogram obtained at the level of the diopter D2 carrying the nanostructures depends only on $R(\lambda)$ and $\phi(\lambda)$; and that the two interference beams F1 and F2 have extremely stable relative phases.

The invention claimed is:

1. An interferometric device comprising:
   a splitter configured to split a collimated incident light beam into a first incident beam and a second incident beam;
   a transparent optical block comprising a set of at least three plane faces, and
   at least one transducer configured to carry out a transduction based on surface plasmon resonance and in contact with a first face;
   wherein a second face carries a network of nanostructures;
   the optical block and the splitter being configured so that the first incident beam undergoes at least one total internal reflection on the first face and the second incident beam undergoes at least one total internal reflection on a third face before they interfere on the second face under total internal reflection;
   the interferometric device further comprising a computer configured to simultaneously compute the spectral distribution of the amplitude and the relative phase of the incident light beam that has interacted with at least one transducer by the first incident beam or by the second incident beam, and
   wherein the first face supports a plurality of transduction zones, each transduction zone comprising an individual transducer.

2. The device according to claim 1, further comprising a second transducer in contact with the third face.

3. The device according to claim 1, wherein the second face comprises a plurality of interference zones, each interference zone comprising a set of nanostructures, the optical block being configured so that a given transduction zone is disposed in correspondence with a given interference zone, so that the total internal reflection of the first incident beam on a given transduction zone interferes with the second incident beam in a given interference zone.

4. The device according to claim 3, wherein the optical block is an assembly or a molding equivalent to an assembly of a first isosceles right prism with a second isosceles right prism, in which a length of a side of the second isosceles right prism is equal to half a length of a hypotenuse of the first isosceles right prism, the second prism being assembled by one of its sides on a half of the hypotenuse of the first prism so that a hypotenuse of the second prism is parallel to a side of the first prism, and so that a cross-section of the optical block produced is inscribed in a square.

5. The device according to claim 4, wherein the splitter is a splitter cube, produced by assembly or by a molding equivalent to the assembly of the first isosceles right prism and of the second isosceles right prism which is identical to the first isosceles right prism, the first isosceles right prism and the second isosceles right prism being assembled by their hypotenuse, one of which is metallized.

6. The device according to claim 5, wherein the position of the central fringe of the interferogram at the convergence point is determined by construction of the optical block as a function of dimensions of the first right isosceles prism and of the second right isosceles prism of the optical block.

7. A spectrometer comprising a device according to claim 5, a light source configured to emit the incident light beam, and an optical sensor disposed opposite the nanostructures of the second face and configured to catch diffusion of the interferogram resulting from the interference of the first incident beam and of the second incident beam.

8. The spectrometer according to claim 7, further comprising:
two power-meters, and
a memory in which a value of power ($P\_mes(\lambda)$) measured by a second power-meter is recorded simultaneously with value of a reference power output by a source measured by a first power-meter; wherein the computer is configured to
determine an incident spectrum by Fourier transform of the interferogram sensed by the optical sensor which measures luminous power diffused by each nanostructure of the network of nanostructures of the second face and store it in a memory;
compute reflectivity ($R\_spr(\lambda)$) according to an equation $R\_spr(\lambda) = 2* P\_mes(\lambda)/ P\_F0(\lambda)$, with $P\_F0(\lambda)$ being power of the incident beam emitted by the light source which is known or measured by the first power-meter.

9. The spectrometer according to claim 8, wherein which the light source is monochromatic, and the computer is configured to compute a phase ($\phi(\lambda)$) of the first beam by computing a difference between two values $I(t1)$ and $I(t0)$ recorded in a memory and corresponding to the interferogram of the first incident beam and of the second incident beam interfering on the second face at a time $t0$ and a later time ($t1$).

10. The spectrometer as according to claim 8, wherein the light source is broadband, and the computer is configured to compute a spectrum of the source filtered by a reflection coefficient ($R\_spr(\lambda)$) of the transducer.

* * * * *